United States Patent
Deuse

(10) Patent No.: US 12,259,074 B2
(45) Date of Patent: Mar. 25, 2025

(54) STERILE CONNECTOR FOR THE STERILE TRANSFER OF A LIQUID MEDIUM

(71) Applicant: Sartorius Stedim Biotech GmbH, Goettingen (DE)

(72) Inventor: Mario Deuse, Bovenden (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 260 days.

(21) Appl. No.: 17/600,729

(22) PCT Filed: Apr. 2, 2020

(86) PCT No.: PCT/EP2020/059437
§ 371 (c)(1),
(2) Date: Oct. 1, 2021

(87) PCT Pub. No.: WO2020/201445
PCT Pub. Date: Oct. 8, 2020

(65) Prior Publication Data
US 2022/0178482 A1     Jun. 9, 2022

(30) Foreign Application Priority Data
Apr. 3, 2019   (DE) ..................... 10 2019 108 664.7

(51) Int. Cl.
*F16L 37/373*   (2006.01)
*B01L 3/00*     (2006.01)

(52) U.S. Cl.
CPC ............. *F16L 37/373* (2013.01); *B01L 3/523* (2013.01); *B01L 2200/026* (2013.01); *B01L 2400/0616* (2013.01)

(58) Field of Classification Search
CPC .................. A61M 39/18; A61M 38/22; A61M 2039/1027; F16L 37/30; F16L 37/373;
(Continued)

(56) References Cited

U.S. PATENT DOCUMENTS

| 407,456 | A | * | 7/1889 | Williams | ............... | F16L 37/373 |
| | | | | | | 285/379 |
| 2,317,827 | A | * | 4/1943 | Townhill | ............... | F16L 37/367 |
| | | | | | | 137/614.01 |

(Continued)

FOREIGN PATENT DOCUMENTS

| DE | 102005030319 A1 * | 1/2007 | .......... A61M 39/165 |
| DE | 102011106852 | 1/2013 | |

(Continued)

OTHER PUBLICATIONS

"International Search Report and Written Opinion," for PCT Application No. PCT/EP2020/059437 mailed Jun. 23, 2020 (7 pages).

(Continued)

*Primary Examiner* — David Colon-Morales
(74) *Attorney, Agent, or Firm* — Pauly, DeVries Smith & Deffner LLC

(57) ABSTRACT

Various embodiments provide a connector for the sterile transfer of a liquid medium from a container to a bioprocess engineering system. The connector has two coupling devices. The coupling devices each have a housing and a control element which is adjustably mounted in the housing interior and forms a channel. The channel extends from a control element inlet opening to a control element outlet opening. The housings are able to be mechanically connected to one another and have a fluid inlet and a fluid outlet. The fluid outlet of one housing and the fluid inlet of the other housing overlap. The control elements are each adjustable from a starting position, into an operating position, in which the control element inlet opening is fluidically connected to the fluid inlet and the control element outlet opening is fluidically connected to the fluid outlet.

19 Claims, 4 Drawing Sheets

(58) Field of Classification Search
CPC ..... F16L 2201/44; F16L 29/002; B01L 3/523; B01L 2200/026; B01L 2400/0644; Y10T 137/87973
USPC ...................................................... 251/149.9
See application file for complete search history.

(56) References Cited

U.S. PATENT DOCUMENTS

| | | | | | |
|---|---|---|---|---|---|
| 2,357,232 | A | * | 8/1944 | Townhill | F16L 37/373 251/309 |
| 2,397,576 | A | * | 4/1946 | Townhill | F16L 37/12 137/599.02 |
| 2,399,525 | A | * | 4/1946 | Waag | F16L 37/56 137/595 |
| 2,440,946 | A | * | 5/1948 | Hansen | F16L 29/002 137/628 |
| 2,828,146 | A | * | 3/1958 | Abbey | F16L 37/12 251/319 |
| 2,872,216 | A | * | 2/1959 | Kaiser | F16L 37/26 251/102 |
| 3,159,180 | A | * | 12/1964 | Courtot | F16L 37/373 137/614.06 |
| 4,335,747 | A | * | 6/1982 | Mitsumoto | F16L 59/18 251/142 |
| 4,438,779 | A | * | 3/1984 | Allread | F16L 37/113 285/85 |
| 4,577,659 | A | * | 3/1986 | Gembus | F16L 25/00 137/637.05 |
| 4,664,149 | A | * | 5/1987 | Fremy | F16L 37/23 137/614.01 |
| 5,083,588 | A | * | 1/1992 | Truchet | F16L 29/04 137/637.05 |
| 5,099,883 | A | * | 3/1992 | Maiville | F16L 37/373 285/87 |
| 5,163,554 | A | * | 11/1992 | Lampropoulos | A61M 25/002 53/469 |
| 5,332,001 | A | * | 7/1994 | Brown | F16L 37/36 251/96 |
| 5,402,825 | A | * | 4/1995 | McCracken | F16L 37/373 137/614.01 |
| 5,488,972 | A | * | 2/1996 | McCracken | F16L 37/36 137/614.01 |
| 5,595,217 | A | * | 1/1997 | Gillen | F16L 37/373 251/111 |
| 5,810,398 | A | * | 9/1998 | Matkovich | A61M 39/18 604/209 |
| 5,884,648 | A | * | 3/1999 | Savage | F16L 37/36 137/614.04 |
| 6,077,259 | A | * | 6/2000 | Caizza | A61M 39/14 604/905 |
| 7,678,096 | B2 | * | 3/2010 | Biddel | F16L 37/26 604/533 |
| 8,128,611 | B2 | * | 3/2012 | Watts | A61M 5/165 604/408 |
| 8,137,332 | B2 | * | 3/2012 | Pipelka | A61M 39/18 604/411 |
| 8,322,368 | B2 | * | 12/2012 | Zenz | F16L 55/1018 137/614.05 |
| 8,449,521 | B2 | * | 5/2013 | Thorne, Jr. | A61J 1/16 604/407 |
| 8,485,356 | B2 | * | 7/2013 | Thorne, Jr. | A61J 1/16 604/3 |
| 8,662,108 | B2 | * | 3/2014 | Haunhorst | F16L 37/0841 251/248 |
| 8,746,278 | B2 | * | 6/2014 | Py | F16L 37/36 251/340 |
| 8,887,762 | B2 | * | 11/2014 | Densel | F16L 37/36 251/149.9 |
| 8,967,177 | B2 | * | 3/2015 | Haunhorst | F16L 37/36 137/614.01 |
| 9,364,653 | B2 | * | 6/2016 | Williams | F16L 37/30 |
| 9,675,520 | B2 | * | 6/2017 | Rogers | B01L 1/02 |
| 9,770,581 | B2 | * | 9/2017 | Gerst | A61M 39/1011 |
| 10,675,454 | B2 | * | 6/2020 | Vigna | A61M 39/18 |
| 10,973,939 | B2 | * | 4/2021 | McLaughlin | B65B 3/003 |
| 11,083,867 | B2 | * | 8/2021 | Otake | A61M 25/002 |
| 2009/0182309 | A1 | | 7/2009 | Muffly | |
| 2010/0130918 | A1 | * | 5/2010 | Elahi | A61M 1/1565 604/29 |
| 2014/0238950 | A1 | * | 8/2014 | Jackson | B65D 51/225 215/247 |
| 2016/0022979 | A1 | | 1/2016 | Vigna et al. | |
| 2017/0314719 | A1 | | 11/2017 | Blake et al. | |
| 2018/0314719 | A1 | | 11/2018 | Subramanian et al. | |
| 2019/0011070 | A1 | | 1/2019 | Fuglsang | |

FOREIGN PATENT DOCUMENTS

| | | | |
|---|---|---|---|
| DE | 102012022144 | 7/2015 | |
| DE | 102015117649 A1 * | 4/2017 | ......... A61M 39/165 |
| WO | 2020201445 | 10/2020 | |

OTHER PUBLICATIONS

"International Standard ISO 14644-1," Cleanrooms and associated controlled environments, Second Edition, Dec. 15, 2015 (44 pages).
"International Preliminary Report on Patentability," for PCT Application No. PCT/EP2020/059437 mailed Sep. 28, 2021 (6 pages).
"Office Action," for German Patent Application No. 102019108664.7 mailed Nov. 21, 2019 (6 pages), no translation.

* cited by examiner

STERILE CONNECTOR FOR THE STERILE TRANSFER OF A LIQUID MEDIUM

CROSS-REFERENCE TO RELATED APPLICATIONS

This application is a national stage application under 35 U.S.C. 371 of International Patent Application Serial No. PCT/EP2020/059437, entitled "Sterile Connector for the Sterile Transfer of a Liquid Medium," filed Apr. 2, 2020, which claims priority from German Patent Application No. DE 10 2019 108 664.7, filed Apr. 3, 2019, the disclosure of which is incorporated herein by reference.

FIELD OF THE TECHNOLOGY

Various embodiments relate to a sterile connector for the sterile transfer of a liquid medium, to a coupling device of a sterile connector, to a packaging arrangement having a packaging and at least one such coupling device sterile packaged therein or such a sterile connector sterile packaged therein, and to the use of such a sterile packaged sterile connector, of such a sterile packaged coupling device and/or of such a packaging arrangement.

BACKGROUND

A bioprocess engineering system is here understood very generally as being a piece of equipment with which biotechnological processes can be carried out or supported. Merely by way of example, mention may be made here of bioreactors, in which microorganisms or tissue cells are cultured under predefined conditions. Such a piece of equipment generally has a container in which there is received a biological reaction medium comprising on the one hand the substances provided for a biotechnological process, for example microorganisms or tissue cells, and on the other hand an appropriate nutrient medium, in order to be able to carry out the biotechnological process step in question, for example fermentation or culturing.

An example of such a bioreactor is on the one hand a production bioreactor, that is to say a relatively large bioreactor on a production scale having a working volume of, for example, several 100 or several 1000 liters, for the industrial production of microbial or cellular products, in particular biopharmaceuticals. Such a bioreactor forms as product a fermentation liquor, which is conventionally treated further in a so-called downstream process to yield a product from the cells or the culture supernatant. Another example is a laboratory bioreactor, that is to say a relatively small bioreactor on a laboratory scale having a working volume of, for example, less than 10 liters. Such a laboratory bioreactor serves, for example, to produce ATMPs (advanced therapy medical products) and/or to perform a cell expansion, by means of which a sufficient number of cells, in particular tissue cells or microbial cells, for the application in question can be produced. An application thereof is the propagation of human cells, for example T-cells (T-lymphocytes), which are taken from the patient, then expanded ex vivo and subsequently reinfused into the patient.

Specifically in the production of ATMPs using a laboratory bioreactor, but in principle also in a production bioreactor, the sterile addition of the individual liquid media, for example biological media, to the bioreactor in question can be particularly important. Since many ATMPs cannot be sterile filtered or finally sterilized, the production of such medical products is carried out in a sterile manner in cleanrooms of appropriate cleanroom classes. Thus the addition of a liquid medium to a bioreactor or the transfer of a liquid medium between two culture vessels and/or bioreactors in principle involves the risk of contamination, and for this reason such handling steps are conventionally carried out in a cleanroom of cleanroom class A (GMP guideline annex 1) or ISO 5 (ISO 14644-1). However, the production of medical products in such cleanrooms is very cost-intensive due to high monitoring requirements, complex gowning procedures, etc.

SUMMARY

For this reason there is a demand for closed systems for the culturing or expansion of cells, in particular in the field of the production of ATMPs, whereby cleanrooms of lower cleanroom classes can be used, for example cleanrooms of cleanroom class D (GMP guideline annex 1) or ISO 8 (ISO 14644-1). However, it is a challenge thereby to add a liquid medium to such a closed system in as simple a way as possible. Although various connection systems such as Luer connectors, Luer-lock connectors, etc. are known for coupling, for example, a minimum-quantity liquid container such as a syringe or vial to a closed system, there is a risk of contamination at the coupling point at which the two coupling devices of the connector, in the case of a Luer connector the male Luer fitting and the female Luer fitting, are connected together, and for this reason particular attention must be paid to sterile conditions when producing the connection.

The problem underlying some aspects of the disclosure is to configure and further develop a sterile connector for the sterile transfer of a liquid medium from a liquid container to a bioprocess engineering system in such a manner that sterile conditions can be established in a simple manner during transfer of the medium.

The above problem is solved in the case of a sterile connector for the sterile transfer of a liquid medium, in particular a biological medium, according to the disclosure.

The fundamental consideration of providing a sterile connector having two coupling devices which are to be connected together for the transfer of liquid from a liquid container, which is, for example, a minimum-quantity liquid container, to a bioprocess engineering system, which in particular is a bioreactor, in which the coupling devices are initially provided in a state in which the parts, such as sterile parts, that are relevant for the transfer of liquid cannot readily be contaminated by the user since, in this state, they are concealed in the coupling device and thus protected against contact.

Specifically, the channel of the coupling device in question and in one coupling device at least the outlet opening and in the other coupling device at least the inlet opening corresponding thereto are in this state in a position that is protected against contamination, such as sterile. Once the two coupling devices have been connected together as intended, they can each be brought into a state in which said parts that are relevant for the transfer of liquid are moved out of the protected, such as sterile position and are connected together and oriented relative to one another in such a manner that the transfer of liquid can take place. In this state permitting the transfer, the previously protected and still sterile outlet opening of one coupling device and the previously protected and still sterile inlet opening of the other coupling device are so arranged relative to one another that the liquid medium is able to flow from one coupling device to the other. In this state, in the region of the transition from one coupling device to the other, the liquid medium comes into contact only with the previously protected and still sterile portions of the coupling devices. Regions that were previously unprotected and accordingly exposed to a possible risk of contamination are at a distance from the region through which fluid flows, so that no germs or other media can enter the liquid medium.

It can be provided if the liquid container from which the medium is to be delivered and/or the bioprocess engineering system to which the medium is to be added are connected in a sterile manner to the respective associated coupling device even before the two coupling devices are connected together. This can be carried out by the manufacturer. Thus it is conceivable that the manufacturer of the liquid container provides the liquid container with the associated coupling device of the sterile connector, wherein the liquid container can be already filled by the manufacturer at this time, wherein the liquid container and the coupling device are made available to the user in the state in which they are connected together as intended, in particular as single-use components. The same also applies to the bioprocess engineering system, in the case of which it is likewise conceivable that the manufacturer of the system provides the system with the associated coupling device of the sterile connector, optionally also with multiple such coupling devices, wherein the bioprocess engineering system and the respective coupling device are made available to the user in the state in which they are connected together as intended, in particular as single-use components.

In this manner, before the connection is produced, the two coupling devices of the sterile connector cannot be contaminated at any, sterile, point that is relevant for the transfer of the liquid, since a sterile connection already exists in the region in which the medium passes from the liquid container into the coupling device associated therewith and also in the region in which the medium passes from the other coupling device into the bioprocess engineering system. The portions of the coupling devices via which the medium passes as intended from the coupling device associated with the liquid container into the respective other coupling device are not moved out of the protected, sterile, region of the respective coupling device and brought together until after the two coupling devices have been connected together. In particular, these two portions are brought together directly, without being able to come into contact with other, contaminable portions of the coupling devices or with the user during their movement from the protected region to their intended end position. Since the parts of the coupling devices that up to this point in time are still sterile are not arranged relative to one another as intended and brought into contact with one another until after the two coupling devices have been connected together, and since contamination of the parts is not possible during this movement, a sterile connection between a liquid container and a bioprocess engineering system can be produced in a particularly simple manner via the proposed sterile connector.

Specifically, it is proposed that the coupling devices each have a housing having a sterile housing interior and a sterile control element which is adjustably mounted in the housing interior and forms a channel, wherein the channel extends through the control element from a control element inlet opening to a control element outlet opening, wherein the housing of one coupling device is able to be mechanically connected to the housing of the other coupling device, wherein each housing has a fluid inlet and a fluid outlet which connect the housing interior to the surroundings, wherein, in the mechanically connected state of the housings, the fluid outlet of one housing and the fluid inlet of the other housing overlap, wherein, in the mechanically connected state of the housings, the control elements are each adjustable from a starting position, in which a fluid connection between the channel and the control element inlet opening on the one hand and between the channel and the control element outlet opening on the other hand is blocked, into an operating position, in which the control element inlet opening is fluidically connected to the fluid inlet and the control element outlet opening is fluidically connected to the fluid outlet.

A "housing" is here understood very generally to be a component which surrounds the control element at least in part, such as substantially completely, in at least one circumferential direction. If the control element, as will be explained in greater detail hereinbelow, is a control element which is rotatably mounted, this control element is surrounded in part or substantially completely by the housing at least based on the axis of rotation in the radial direction. The latter can be especially when the control element inlet openings and control element outlet openings face radially outwards, based on the axis of rotation. However, it is in principle also conceivable that the control element inlet openings and control element outlet openings face parallel to the axis of rotation, wherein in this case the control element can be surrounded in the axial direction by the housing at least in part or substantially completely. In principle, the control element can also be linearly movable, wherein the housing then surrounds the control element such as on the sides parallel to the direction of movement at least in part or substantially completely, wherein in this case the control element inlet openings and the control element outlet openings of the control elements are oriented in a direction transverse to the direction of movement.

"Substantially completely" means that the housing is here closed completely in the direction in question except for the fluid inlet and the fluid outlet.

The housing is in any case so configured that it protects the control element inlet opening and the control element outlet opening in the starting position of the control element and thus keeps them sterile, and in the operating position of the control element allows the control element outlet opening of one coupling device, which in particular is associated with the liquid container, and the control element inlet opening of the other coupling device, which in particular is associated with the bioprocess engineering system, to be brought to overlap.

"Overlap" here means partial or complete overlapping of the two openings in a direction parallel to the center axes of the openings.

Various embodiments provide possible ways in which, in the starting position, the sterile control element inlet openings and the sterile control element outlet openings can be arranged in the housings so that they are protected optimally with respect to the surroundings and against contamination, and in which they can be arranged relative to one another in the operating position while maintaining sterility. To this end there is provided in each housing in particular a hermetically sealed region, which can be already sterile in the delivery condition, in which the channel running through the control element extends in the starting position of the control element. Only by a movement of the control element from its starting position into its operating position would the channel, and accordingly its control element inlet opening or control element outlet opening, move into a non-sterile region. However, when the sterile connector is used as intended, the two coupling devices are connected together beforehand in such a manner that the movement of the control element from the starting position into the operating position cannot lead to contact of the control element inlet opening, the control element outlet opening and the channel with the surroundings.

"Hermetically tight" or "hermetically sealed" means in this context that tightness that prevents the ingress of impurities, in particular germs, is provided. In a further embodiment, "hermetically tight" or "hermetically sealed" refers to a region of the sterile connector that is sterile and/or protected against contamination. In various embodiments, the terms "hermetically tight" and "hermetically sealed" likewise encompass the term "sterile" and are thus interchangeable.

Various embodiments relate to orientations of all the parts through which fluid flows in the operating position of each control element. In some embodiments, the two fluid inlets of the housings, the two fluid outlets of the housings and the two channels of the control elements run coaxially with one another. However, other paths are in principle also conceivable here.

Various embodiments relate to the adjusting movement of each control element between the starting position and the operating position. In particular, the adjusting movement of one control element is accompanied by a corresponding adjusting movement of the other control element, that is to say, the two control elements move synchronously and are simultaneously in their starting positions and simultaneously in their operating positions. This is made possible via a transmission, in particular a gear train. The transmission can be actuated by the user from outside the housing, whereby the adjusting movements of the two control elements are effected.

According to some embodiments, the fluid inlet of one housing and the fluid outlet of the other housing are able to be connected or are connected by a flexible tube or a pipe. As already explained hereinbefore, it can be provided if the liquid container is connected to the respective associated one coupling device and the bioprocess engineering system is connected to the respective associated other coupling device by the manufacturer, which can likewise take place via a corresponding flexible tube or a corresponding pipe.

Various embodiments provide possible ways of connecting the two housings together.

According to some embodiments, a coupling device of a sterile connector, in particular of a proposed sterile connector, for the sterile transfer of a liquid medium, in particular a biological medium, from a liquid container to a bioprocess engineering system, in particular to a bioreactor, is provided. In light of the fact that the proposed sterile connector has two coupling devices, reference may be made to all relevant remarks concerning the first-mentioned teaching.

According to some embodiments, a packaging arrangement having a packaging and having at least one, such as exactly one, proposed coupling device sterile packaged therein or a proposed sterile connector sterile packaged therein is provided. In light of the fact that the proposed packaging arrangement has a proposed sterile connector or a proposed coupling device, reference may be made to all relevant remarks concerning the first-mentioned and the second-mentioned teaching.

According to some embodiments, either a liquid container or a bioprocess engineering system can additionally be sterile packaged in the packaging, wherein the liquid container or the bioprocess engineering system is already fluidically coupled with the coupling device in the packaging.

According to some embodiments, the use of a sterile packaged proposed sterile connector, of a sterile packaged proposed coupling device and/or of a proposed packaging arrangement for the sterile transfer of a liquid medium, in particular a biological medium, from a liquid container to a bioprocess engineering system, in particular to a bioreactor, is provided. In light of the fact that the proposed use relates to the use of a proposed sterile connector, of a proposed coupling device and/or of a proposed packaging arrangement, reference may be made to all relevant remarks concerning the above-mentioned teachings.

With the proposed packaging arrangement and the proposed use it has been recognized that, with the proposed sterile connector or with the proposed coupling devices, a liquid medium can be fed in a particularly simple manner into a closed system, in particular a bioreactor, without any appreciable risk of contamination, in that the coupling devices maintain the parts that are relevant for the liquid transfer in a sterile state, namely in said starting position, until the liquid transfer, namely in said operating position, actually takes place.

In various embodiments, some of the mentioned components, in particular the proposed coupling device, in particular both coupling devices, also the liquid container and/or the bioprocess engineering system and/or the flexible tube(s) or the pipe(s), can be in the form of single-use components, wherein the components can be produced from a plastics material.

Various embodiments provide a sterile connector for the sterile transfer of a liquid medium, in particular a biological medium, from a liquid container to a bioprocess engineering system, in particular to a bioreactor, wherein the sterile connector has two coupling devices, wherein the coupling devices each have a housing having a housing interior and a control element which is adjustably mounted in the housing interior and forms a channel, wherein the channel extends through the control element from a control element inlet opening to a control element outlet opening, wherein the housing of one coupling device is able to be mechanically connected to the housing of the other coupling device, wherein each housing has a fluid inlet and a fluid outlet which connect the housing interior to the surroundings, wherein, in the mechanically connected state of the housings, the fluid outlet of one housing and the fluid inlet of the other housing overlap, wherein, in the mechanically connected state of the housings, the control elements are each adjustable from a starting position, in which a fluid connection between the channel and the control element inlet opening on the one hand and between the channel and the control element outlet opening on the other hand is blocked, into an operating position, in which the control element inlet opening is fluidically connected to the fluid inlet and the control element outlet opening is fluidically connected to the fluid outlet.

In various embodiments, in the starting position, each channel extends in a region of the housing interior that is hermetically sealed with respect to the surroundings of the housing, wherein, in the starting position, the control element inlet opening and the control element outlet opening each face the housing inner wall of the respective housing.

In various embodiments, in the starting position, a portion, in particular a circumferential portion, of the respective control element closes the fluid inlet and/or a portion, in particular a circumferential portion, of the respective control element closes the fluid outlet of the respective housing in a hermetically tight manner, and/or wherein, in the starting position, a portion, in particular a circumferential portion, of the respective control element extending around the control element inlet opening and/or a portion, in particular a circumferential portion, of the respective control element extending around the control element outlet opening is in contact in a hermetically sealing manner with the housing inner wall of the respective housing, and/or wherein, in the starting position, a portion of the respective housing extending around the fluid inlet and/or a portion of the respective housing extending around the fluid outlet is in contact in a hermetically sealing manner with the respective control element.

In various embodiments, the control element of one housing projects from the housing interior through the fluid outlet of the housing, and/or wherein the control element of the other housing projects from the housing interior through the fluid inlet of the housing.

In various embodiments, the control element of one housing and the control element of the other housing, in the mechanically connected state of the housings, at least when the two control elements are in their operating position, also when the two control elements are in their starting position, in some embodiments always, are in contact with one another under preload, wherein the control elements deform elastically in the region of mutual contact.

In various embodiments, in the mechanically connected state of the housings, when the two control elements are in their operating position, a portion, in particular a circumferential portion, of one control element extending around the control element outlet opening and a portion, in particular a circumferential portion, of the other control element extending around the control element inlet opening are in contact with one another in such a manner that the respective channel is hermetically sealed with respect to the respective housing.

In various embodiments, each control element is produced in part or completely, in particular in the portion that closes the fluid inlet in a hermetically tight manner, and/or in the portion that closes the fluid outlet in a hermetically tight manner, and/or in the portion extending around the control element inlet opening and/or in the portion extending around the control element outlet opening, from an elastomer, in particular from a silicone material, and/or wherein each housing is produced in part, in particular in the portion extending around the fluid inlet and/or in the portion extending around the fluid outlet, from an elastomer, in particular from a silicone material, and for the rest from a plastics material with relatively low elasticity, in particular from a thermoplastic.

In various embodiments, in the mechanically connected state of the housings, when the two control elements are in their operating position, in the case of both coupling devices in each case the fluid inlet and the control element inlet opening and/or the fluid outlet and the control element outlet opening overlap, in particular are oriented coaxially with one another, and the fluid outlet of one housing and the fluid inlet of the other housing overlap, in particular are oriented coaxially with one another, wherein, in the mechanically connected state of the housings, when the two control elements are in their operating position, the two fluid inlets, the two fluid outlets and the two channels are oriented coaxially with one another.

In various embodiments, in the mechanically connected state of the housings, an adjusting movement of one control element between its starting position and its operating position is accompanied by a corresponding adjusting movement of the other control element, wherein there is provided a transmission, in particular a gear train, which, in the mechanically connected state of the housings, effects a synchronous adjustment of the two control elements between their starting position and their operating position, wherein a transmission component of the transmission, in particular a gear wheel or gear wheel segment of the transmission, is connected or is able to be connected in a rotationally fixed manner to an actuating element.

In various embodiments, the adjusting movement of each control element between its starting position and its operating position is a rotational movement or a linear movement.

In various embodiments, the adjusting movement of each control element between its starting position and its operating position is limited in the starting position and/or operating position via a stop.

In various embodiments, the fluid inlet of one housing and the fluid outlet of the other housing is able to be connected or is connected, in particular via a plug-in connection, to a flexible tube or a pipe, wherein the fluid inlet of one housing is fluidically coupled via the flexible tube or the pipe with a liquid container, in particular with a minimum-quantity liquid container, for the delivery of a liquid medium, in particular a biological medium, and/or wherein the fluid outlet of the other housing is fluidically coupled via the flexible tube or the pipe with a bioprocess engineering system, in particular a bioreactor.

In various embodiments, the two housings are able to be connected together in a form-fitting manner, in particular are able to be pushed together or latched together.

Various embodiments provide a coupling device of a sterile connector for the sterile transfer of a liquid medium, in particular a biological medium, from a liquid container to a bioprocess engineering system, in particular to a bioreactor, in particular a sterile connector as provided herein, wherein the coupling device has a housing having a housing interior and a control element which is adjustably mounted in the housing interior and forms a channel, wherein the channel extends through the control element from a control element inlet opening to a control element outlet opening, wherein the housing of the coupling device is able to be mechanically connected to the housing of a further coupling device of the sterile connector, wherein the housing has a fluid inlet and a fluid outlet which connect the housing interior to the surroundings, wherein, in the mechanically connected state of the housings, the fluid outlet of the housing of the coupling device and the fluid inlet of the housing of the further coupling device are able to be brought to overlap, wherein, in the mechanically connected state of the housings, the control element is adjustable from a starting position, in which a fluid connection between the channel and the control element inlet opening on the one hand and between the channel and the control element outlet opening on the other hand is blocked, into an operating position, in which the control element inlet opening is fluidically connected to the fluid inlet and the control element outlet opening is fluidically connected to the fluid outlet.

Various embodiments provide a packaging arrangement having a packaging and having at least one, in some embodiments exactly one, coupling device as described herein sterile packaged therein or a sterile connector as described herein sterile packaged therein.

In various embodiments, the control element of the coupling device sterile packaged in the packaging is in its starting position, and wherein there is additionally sterile packaged in the packaging a liquid container, in particular a filled liquid container, which is fluidically coupled with the coupling device, or there is sterile packaged a bioprocess engineering system which is fluidically coupled with the coupling device.

Various embodiments provide a use of a sterile packaged sterile connector as described herein, of a sterile packaged coupling device as described herein and/or of a packaging arrangement as described herein for the sterile transfer of a liquid medium, in particular a biological medium, from a liquid container to a bioprocess engineering system, in particular to a bioreactor.

In various embodiments, at least one coupling device, in particular both coupling devices, also the liquid container and/or the bioprocess engineering system and/or the flexible tube(s) or the pipe(s), in particular as a single-use component, are produced at least in part, in some embodiments at least predominantly, from a plastics material.

BRIEF DESCRIPTION OF THE DRAWINGS

Various aspects will be explained in greater detail herein below with reference to a drawing illustrating only one exemplary embodiment. In the drawing.

DETAILED DESCRIPTION

Figure 1:
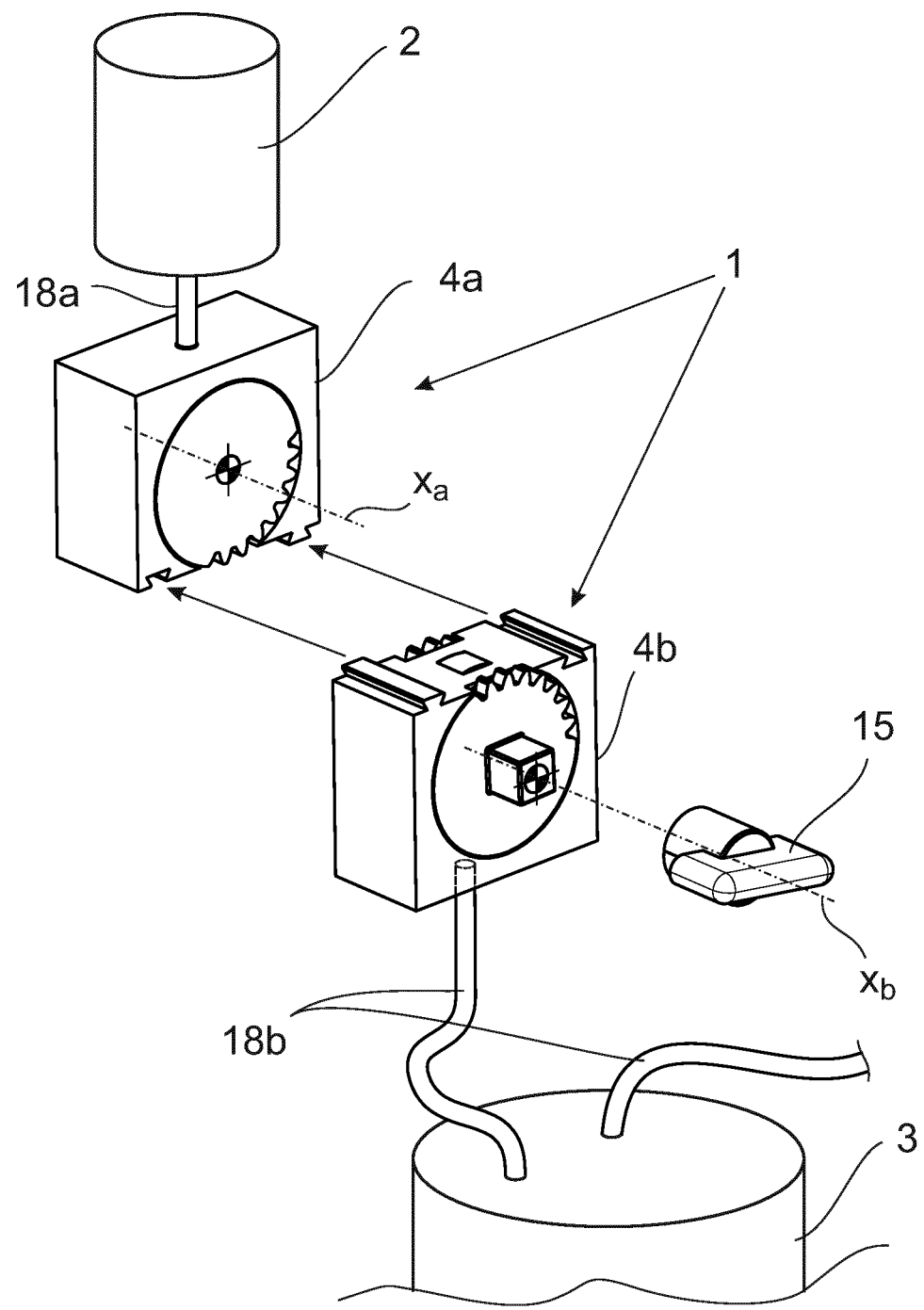
FIG. 1 shows, in a perspective view, a proposed sterile connector during connection of its two coupling devices.

The proposed sterile connector 1 illustrated in FIGS. 1 to 4 serves for the sterile transfer of a liquid medium, in particular a biological medium, from a liquid container 2, here a minimum-quantity liquid container, that is to say a liquid container having a small capacity of, for example, not more than 30 ml, to a bioprocess engineering system 3, here to a bioreactor. The proposed sterile connector 1 has two coupling devices 4a, 4b which are able to be mechanically and fluidically connected together, of which one coupling device 4a is associated with the liquid container 2 and the other coupling device 4b is associated with the bioprocess engineering system 3. "Associated" means that the coupling device 4a is able to be connected or is connected to the liquid container 2 and the coupling device 4b is able to be connected or is connected to the bioprocess engineering system 3. In some embodiments, on the one hand the liquid container 2 has already been connected to the associated coupling device 4a and the bioprocess engineering system 3 has already been connected to the associated coupling device 4b by the manufacturer, namely in the sterile state.

The bioprocess engineering system 3, in particular the bioreactor, here forms a closed system or is integrated into a closed system. The bioreactor is, for example, in the form of a laboratory bioreactor, that is to say a bioreactor which, in contrast to a production bioreactor, has a relatively small working volume (maximum available filling volume) of not more than 10 liters. Such a bioreactor is used for carrying out a biotechnological process and for producing an advanced therapy medical product (ATNF). For example, the biotechnological process may also be a cell expansion process for T-cells. In any case, a biological reaction medium which comprises in particular tissue cells or microbial cells and also a nutrient medium is provided in the bioreactor. It is thereby necessary to add the liquid media to the closed system in a sterile manner.

The coupling devices 4a, 4b each can have a housing 5a, 5b having a sterile housing interior 6a, 6b and a sterile control element 8a, 8b which is adjustably mounted in the housing interior 6a, 6b and forms a channel 7a, 7b, wherein the channel 7a, 7b extends through the control element 8a, 8b from a control element inlet opening 9a, 9b to a control element outlet opening 10a, 10b. It is further possible that the housing 5a of one coupling device 4a is able to be mechanically connected to the housing 5b of the other coupling device 4b. It is also possible that each housing 5a, 5b has a fluid inlet 11a, 11b and a fluid outlet 12a, 12b which connect the housing interior 6a, 6b to the surroundings of the respective housing 5a, 5b, wherein, in the mechanically connected state of the housings 5a, 5b, the fluid outlet 12a of one housing 5a and the fluid inlet 11b of the other housing 5b overlap. Finally, it is also possible that, in the mechanically connected state of the housings 5a, 5b, the control elements 8a, 8b are each adjustable from a starting position (FIG. 2a), FIG. 3a)), in which a fluid connection between the channel 7a, 7b and the control element inlet opening 9a, 9b on the one hand and between the channel 7a, 7b and the control element outlet opening 10a, 10b on the other hand is blocked, into an operating position (FIG. 2b), FIG. 3b)), in which the control element inlet opening 9a, 9b is fluidically connected to the fluid inlet 11a, 11b and the control element outlet opening 10a, 10b is fluidically connected to the fluid outlet 12a, 12b, in particular completely.

In the proposed sterile connector 1, or the proposed coupling devices 4a, 4b which are to be connected together, it is thus provided that the control elements 8a, 8b can be moved from a starting position into an operating position, wherein in the starting position the parts that are relevant for the fluid transfer, namely the channel 7a, 7b, the control element inlet opening 9a, 9b and/or the control element outlet opening 10a, 10b, are in a sterile state. The sterile state is ensured in that the parts that are relevant for the fluid transfer, in the starting position of the control element 8a, 8b, can be sterile and covered with respect to the surroundings of the housing 5a, 5b and accordingly protected against contamination. If the two coupling devices 4a, 4b are connected together as intended, the control elements 8a, 8b are able to move into the operating position, in which the transfer of the liquid medium can then take place. In the operating position, said parts that are relevant for the fluid transfer are still sterile, since the two coupling devices 4a, 4b, or the two housings 5a, 5b, were connected together beforehand, that is to say before the movement from the starting position into the operating position, in such a manner that the parts that are relevant for the fluid transfer could not come into contact with the surroundings at any time.

In the exemplary embodiment illustrated here, each channel 7a, 7b extends in the starting position in a region of the housing interior 6a, 6b that is hermetically sealed with respect to the surroundings of the housing 5a, 5b and that is already sterile here in the delivery state. Furthermore, here, the control element inlet opening 9a, 9b and the control element outlet opening 10a, 10b each face the housing inner wall 13a, 13b of the respective housing 5a, 5b in the starting position.

Figure 3:
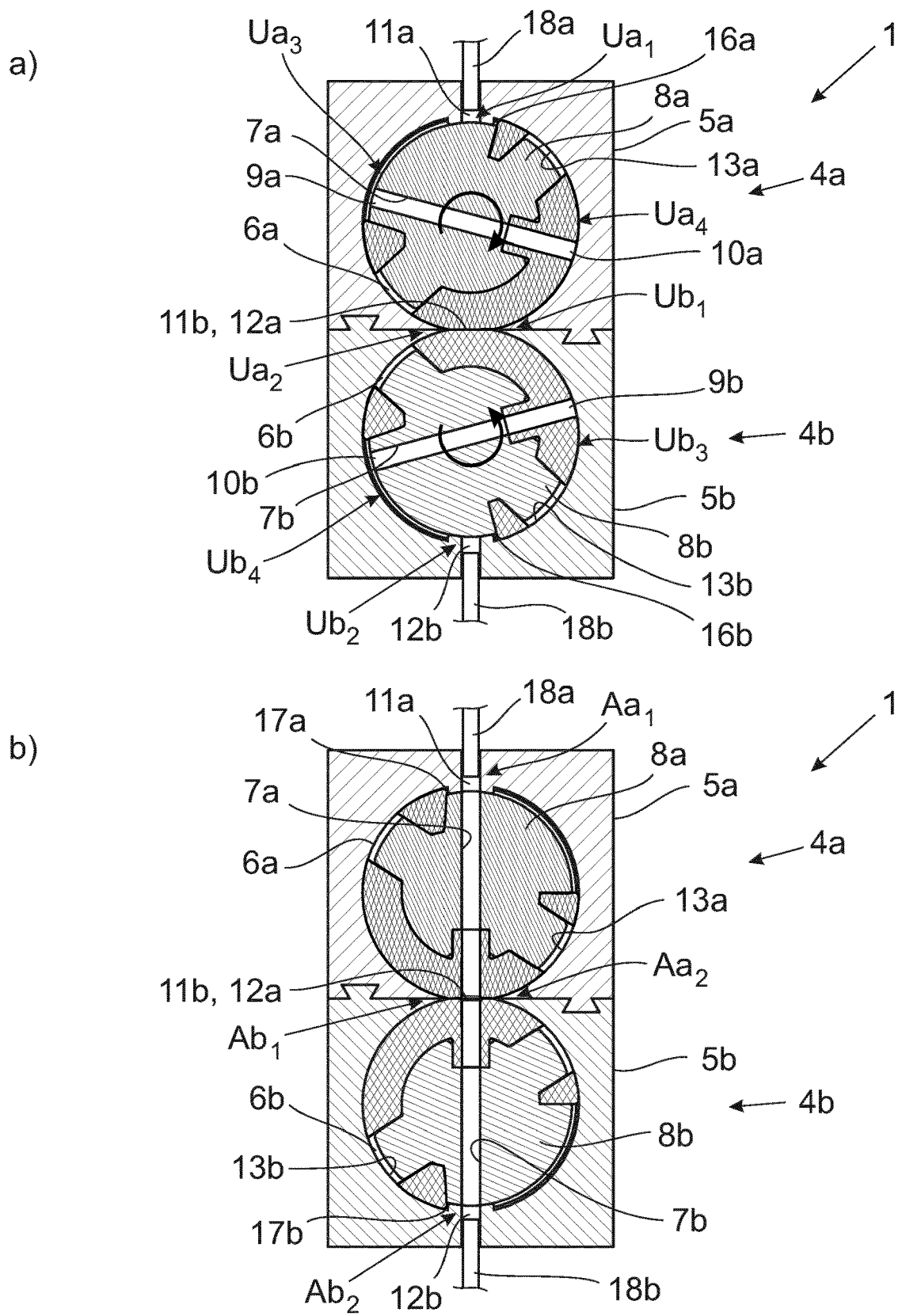
FIG. 3 shows, in a cutaway view, the two coupling devices in the connected state a) in the starting position of the two control elements and b) in the operating position of the two control elements.

Each control element 8a, 8b is here a control element which is rotatably mounted and, as shown in FIG. 3, has a substantially round cross section. Correspondingly, each control element 8a, 8b has a substantially cylindrical circumference extending around the axis of rotation $x_a$, $x_b$ of the control element 8a, 8b, wherein the respective control element inlet opening 9a, 9b and the respective control element outlet opening 10a, 10b are here arranged on the circumference and face in the radial direction, based on the axes of rotation $x_a$, $x_b$. The channel 7a, 7b connecting the respective control element inlet opening 9a, 9b to the respective control element outlet opening 10a, 10b has here a linear path. The channel here runs centrally through the respective control element 8a, 8b, that is to say also through the axis of rotation $x_a$, $x_b$ of the respective control element 8a, 8b. The control element inlet opening 9a, 9b and the control element outlet opening 10a, 10b of the respective control element 8a, 8b here lie diametrically opposite one another. In an alternative exemplary embodiment not shown here, it is also conceivable that the control element inlet opening and/or control element outlet opening of the control element 8a, 8b can be oriented laterally, that is to say parallel to the axis of rotation $x_a$, $x_b$. In addition or alternatively, it is also conceivable in a further exemplary embodiment not shown here to provide a linearly movable control element instead of a rotatable control element 8a, 8b. The remarks concerning the control elements 8a, 8b which are here rotatable accordingly equally apply also to control elements that are otherwise configured or adjustable, in particular also to linearly adjustable control elements.

The fluid inlet 11a of one housing 5a and the fluid outlet 12b of the other housing 5b is here channel-shaped, that is to say is in the form of an inlet or outlet channel leading from outside into the housing interior 6a, 6b, whereas the fluid outlet 12a of one housing 5a and the fluid inlet 11b of the other housing 5b is here in the form of an opening which connects the housing interior 6a, 6b directly to the surroundings. In one exemplary embodiment, the cross section of the fluid inlet 11a of one housing 5a and of the fluid outlet 12b of the other housing 5b is smaller than the cross section of the fluid outlet 12a of one housing 5a and of the fluid inlet 11b of the other housing 5b. The "cross section" is always based on a section transverse to the direction of flow. The longitudinal extent of the fluid inlet 11a of one housing 5a and of the fluid outlet 12b of the other housing 5b is here additionally larger than the longitudinal extent of the fluid outlet 12a of one housing 5a and of the fluid inlet 11b of the other housing 5b. The latter is approximately zero. The "longitudinal extent" is always based on the direction of flow.

Furthermore, here, in the starting position, a portion, in particular a circumferential portion $Ua_1$, $Ub_1$, of the respective control element 8a, 8b closes the fluid inlet 11a, 11b of the respective housing 5a, 5b in a hermetically tight manner. In addition or alternatively, it is here further provided that, in the starting position, a further portion, in particular a further circumferential portion $Ua_2$, Ube, of the respective control element 8a, 8b closes the fluid outlet 12a, 12b of the respective housing 5a, 5b in a hermetically tight manner.

Furthermore, here, in the starting position, a portion, in particular a circumferential portion $Ua_3$, $Ub_3$, of the respective control element 8a, 8b extending around the control element inlet opening 9a, 9b is in contact in a hermetically sealing manner with the housing inner wall 13a, 13b of the respective housing 5a, 5b. In addition or alternatively, it is here provided that, in the starting position, a portion, in particular a circumferential portion $Ua_4$, $Ub_4$, of the respective control element 8a, 8b extending around the control element outlet opening 10a, 10b is in contact in a hermetically sealing manner with the housing inner wall 13a, 13b of the respective housing 5a, 5b.

Moreover, here, in the starting position, a portion $Aa_1$, extending around the fluid inlet 11a, of the housing 5a of the coupling device 4a that is here associated with the liquid container 2 and/or a portion $Ab_2$, extending around the fluid outlet 12b, of the housing 5b of the coupling device 4b that is here associated with the bioprocess engineering system 3 is in contact in a hermetically sealing manner with the respective control element 8a, 8b, namely the portion $Aa_1$ with the control element 8a and the portion $Ab_2$ with the control element 8b. Here, it is further provided that, in the starting position, a portion $Aa_2$, extending around the fluid outlet 12a, of the housing 5a of the coupling device 4a that is here associated with the liquid container 2 and/or a portion $Ab_1$, extending around the fluid inlet 11b, of the housing 5b of the coupling device 4b that is here associated with the bioprocess engineering system 3 is in contact in a hermetically sealing manner with the respective control element 8a, 8b.

As is shown in particular by FIGS. 3a) and 3b), the control element 8a of one housing 5a and the control element 8b of the other housing 5b are in contact with one another under preload in the mechanically connected state of the housings 5a, 5b at least when the two operating elements 8a, 8b are in their operating position, here also when the two operating elements 8a, 8b are in their starting position. Here, the two control elements 8a, 8b are always in contact with one another under preload. This is achieved in particular in that the control elements 8a, 8b are produced either completely or at least only in the region of their mutual contact from a comparatively flexible plastics material, in particular from an elastomer, in particular from a silicone material. In this manner, the control elements 8a, 8b are able to deform elastically in the region of mutual contact. As is shown in FIG. 3, here, in the mechanically connected state of the housings 5a, 5b, when the two control elements 8a, 8b are in their operating position, a portion, in particular a circumferential portion $Ua_4$, of one control element 8a extending around the control element outlet opening 10a and a portion, in particular a circumferential portion $Ub_3$, of the other control element 8b extending around the control element inlet opening 9b are in contact with one another in such a manner that the respective channel 7a, 7b is hermetically sealed with respect to the respective housing 5a, 5b.

For the purpose of hermetic sealing, there is provided in particular an elastomer, as mentioned. In some embodiments, each control element 8a, 8b is produced in part or completely from such an elastomer, in particular from a silicone material. Each housing 5a, 5b can also be produced, at least in part, from an elastomer, in particular from a silicone material, although it can be that the housing 5a, 5b is produced from a plastics material with as little elasticity as possible, such as from a plastics material with relatively low elasticity, in particular a thermoplastic or Vero material. According to some embodiments, it is provided that each control element 8a, 8b is produced in part or completely, in particular in the portion, here the circumferential portion $Ua_1$, $Ub_1$, that closes the fluid inlet 11a, 11b in a hermetically tight manner, and/or in the portion, here the circumferential portion $Ua_2$, Ube, that closes the fluid outlet 12a, 12b in a hermetically tight manner, and/or in the portion, here the circumferential portion $Ua_3$, $Ub_3$, that extends around the control element inlet opening 9a, 9b, and/or in the portion, here the circumferential portion $Ua_4$, $Ub_4$, that extends around the control element outlet opening 10a, 10b, from an elastomer, in particular from a silicone material. In addition or alternatively, it can be provided that each housing 5a, 5b is produced in part, in particular in the portion $Aa_1$, $Ab_1$ extending around the fluid inlet 11a, 11b and/or in the portion $Aa_2$, Abe extending around the fluid inlet 12a, 12b, from an elastomer, in particular from a silicone material, and in some embodiments for the rest from a plastics material with relatively low elasticity, in particular a thermoplastic or Vero material.

As is further illustrated in FIG. 3b), in the mechanically connected state of the housings 5a, 5b, when the two control elements 8a, 8b are in their operating position, in the case of the coupling devices 4a, 4b in each case the fluid inlet 11a, 11b and the control element inlet opening 9a, 9b on the one hand and/or the fluid outlet 12a, 12b and the control element outlet opening 10a, 10b on the other hand overlap. In particular, they are oriented coaxially with one another. At the same time, the fluid outlet 12a of one housing 5a and the fluid inlet 11b of the other housing 5b overlap. They too are here oriented coaxially with one another. In some embodiments, as shown in FIG. 3b), the two fluid inlets 11a, 11b, the two fluid outlets 12a, 12b and the two channels 7a, 7b are here oriented coaxially with one another.

Figure 2:
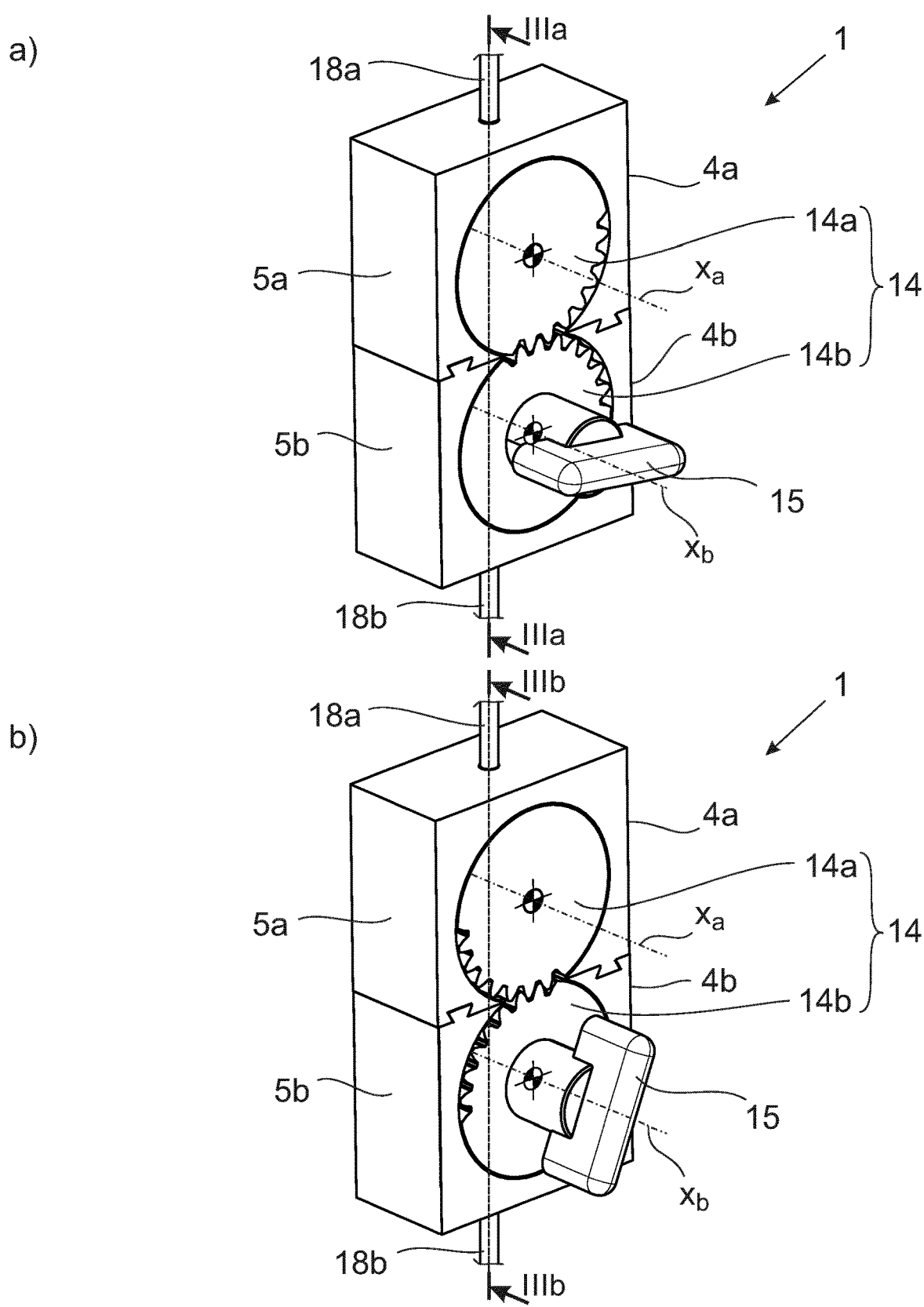
FIG. 2 shows, in a perspective view, the two coupling devices in the connected state a) in the starting position of the two control elements and b) in the operating position of the two control elements.

The adjusting movement, illustrated in FIG. 3a) by a circular arrow, of one control element 8a between its starting position and its operating position is here accompanied by a corresponding adjusting movement of the other control element 8b. This can apply here only for the mechanically connected state of the housings 5a, 5b, as is illustrated in FIGS. 2 and 3. For this purpose, a transmission 14 is here provided, which transmission, as shown in FIG. 2, can be a gear train 14. The transmission 14 has at least two transmission components, in some embodiments each in the form of a gear wheel and/or gear wheel segment 14a, 14b. There is here provided as the gear wheel segment 14a, 14b, for example, a toothed circumferential portion of a circular disk, wherein, instead of a disk having a full circumference as here, the disk may also be in the form of only a sector of a circle, wherein the toothing then extends along the circular arc. Here, two gear wheel segments 14a, 14b are provided as transmission components. In the mechanically connected state of the housings 5a, 5b, the transmission 14 effects a synchronous adjustment of the two control elements 8a, 8b between their starting position and their operating position. In addition, a transmission component of the transmission 14, in particular a gear wheel or gear wheel segment 14b of the transmission 14, is here connected or able to be connected in a rotationally fixed manner to an actuating element 15 for manually actuating the transmission 14. The actuating element 15 can be a lever, a crank or the like.

The adjusting movement of each control element 8a, 8b between the starting position and the operating position is here a rotational movement, as indicated hereinbefore, that is to say the control element 8a, 8b is here in each case a rotatable control element. Each control element 8a, 8b is here adjusted between the starting position and the operating position in an angle of less than 45 degrees, of less than 40 degrees, of less than 35 degrees, or less than 30 degrees. In principle, in an alternative exemplary embodiment not illustrated here, a linear movement of each control element is also conceivable as the adjusting movement, as mentioned.

The adjusting movement of each control element 8a, 8b can be limited in one or both directions, that is to say towards the starting position and/or towards the operating position. Here, this is ensured in both directions in that at least one transmission component, here both transmission components, is or are a gear wheel segment 14a, 14b, so that an adjusting movement is possible only in the toothed circumferential portion, that is to say, for example, only in an angle range of less than 45 degrees, of less than 40 degrees, of less than 35 degrees, or of less than 30 degrees. In addition or alternatively, as is shown merely by way of example in FIGS. 3a) and b), the adjusting movement can be limited in the starting position via a stop 16a, 16b and/or in the operating position via a stop 17a, 17b. The respective stop 16a, 16b and/or the respective stop 17a, 17b can be provided inside the housing 5a, 5b, as is the case here, or also outside the housing 5a, 5b.

In this manner, the starting position can initially be set as the defined position, in particular by the manufacturer, so that it is reliably ensured that the parts that are relevant for the fluid transfer are in the protected and in particular sterile region. Then, the operating position can be set as the defined position, in particular by the user, so that it is reliably ensured that each control element inlet opening 9a, 9b overlaps the respective associated fluid inlet 11a, 11b and each control element outlet opening 10a, 10b overlaps the respective associated fluid outlet 12a, 12b.

FIGS. 1 and 2 further show that the fluid inlet 11a of one housing 5a and the fluid outlet 12b of the other housing 5b are here able to be connected or are connected, in particular via a plug-in connection, in each case to a flexible tube 18a, 18b or a pipe. Here, the fluid inlet 11a of one housing 5a is coupled via a flexible tube 18a or a pipe with the liquid container 2. In addition or alternatively, as is likewise shown in FIGS. 1 and 2, the fluid outlet 12b of the other housing 5b is fluidically coupled via a flexible tube 18b or a pipe with the bioprocess engineering system 3, here the bioreactor.

It can further be seen from FIGS. 1 to 3 that the housings 5a, 5b are able to be connected to one another in a form-fitting manner. Here, merely by way of example, they are able to pushed together, for example via a dovetail connection or the like. However, it is in principle also conceivable that the housings 5a, 5b are able to be latched together. It can be that only the housings 5a, 5b are securely held together when the adjusting movement of the control elements 8a, 8b is carried out. Since the control elements, at least in the operating position, can be in contact with one another under preload, the form-fitting connection can likewise exists in the direction of the preload. Here, the form-fitting connection between the housings 5a, 5b is present in the direction of flow of the liquid medium on transfer thereof.

According to various embodiments, each coupling device 4a, 4b, that is to say here the coupling device 4a associated with the liquid container 2 and/or the coupling device 4b associated with the bioprocess engineering system 3, is provided as such. In particular, the coupling device 4a, 4b is a coupling device of the proposed sterile connector 1.

Such a coupling device 4a has a housing 5a having a housing interior 6a and a control element 8a which is adjustably mounted in the housing interior 6a and forms a channel 7a, wherein the channel 7a extends through the control element 8a from a control element inlet opening 9a to a control element outlet opening 10a. The housing 5a of the coupling device 4a is able to be mechanically connected to the housing 5b of a further coupling device 4b, wherein reference may be made with regard to the configuration of the further coupling device 4b to the remarks concerning the proposed first coupling device 4a. The housing 5a has a fluid inlet 11a and a fluid outlet 12a which connect the housing interior 6a to the surroundings, wherein, in the mechanically connected state of the housings 5a, 5b, the fluid outlet 12a of the housing 5a of the proposed coupling device 4a and the fluid inlet 11b of the housing 5b of the further coupling device 4b are able to be brought to overlap. In the mechanically connected state of the housings 5a, 5b, the control element 8a is adjustable from a starting position, in which a fluid connection between the channel 7a and the control element inlet opening 9a on the one hand and between the channel 7a and the control element outlet opening 10a on the other hand is blocked, into an operating position, in which the control element inlet opening 9a is fluidically connected to the fluid inlet 11a and the control element outlet opening 10a is fluidically connected to the fluid outlet 12a. In this respect, reference may be made to all remarks concerning the proposed sterile connector 1.

According to various embodiments, a packaging arrangement 19, 21 having a packaging 20, 22 and having at least one, such as exactly one, proposed coupling device 4a, 4b sterile packaged therein or a proposed sterile connector 1 sterile packaged therein is provided. In this respect, reference may be made to all remarks concerning the proposed sterile connector 1 and the proposed coupling device 4a.

Figure 4:
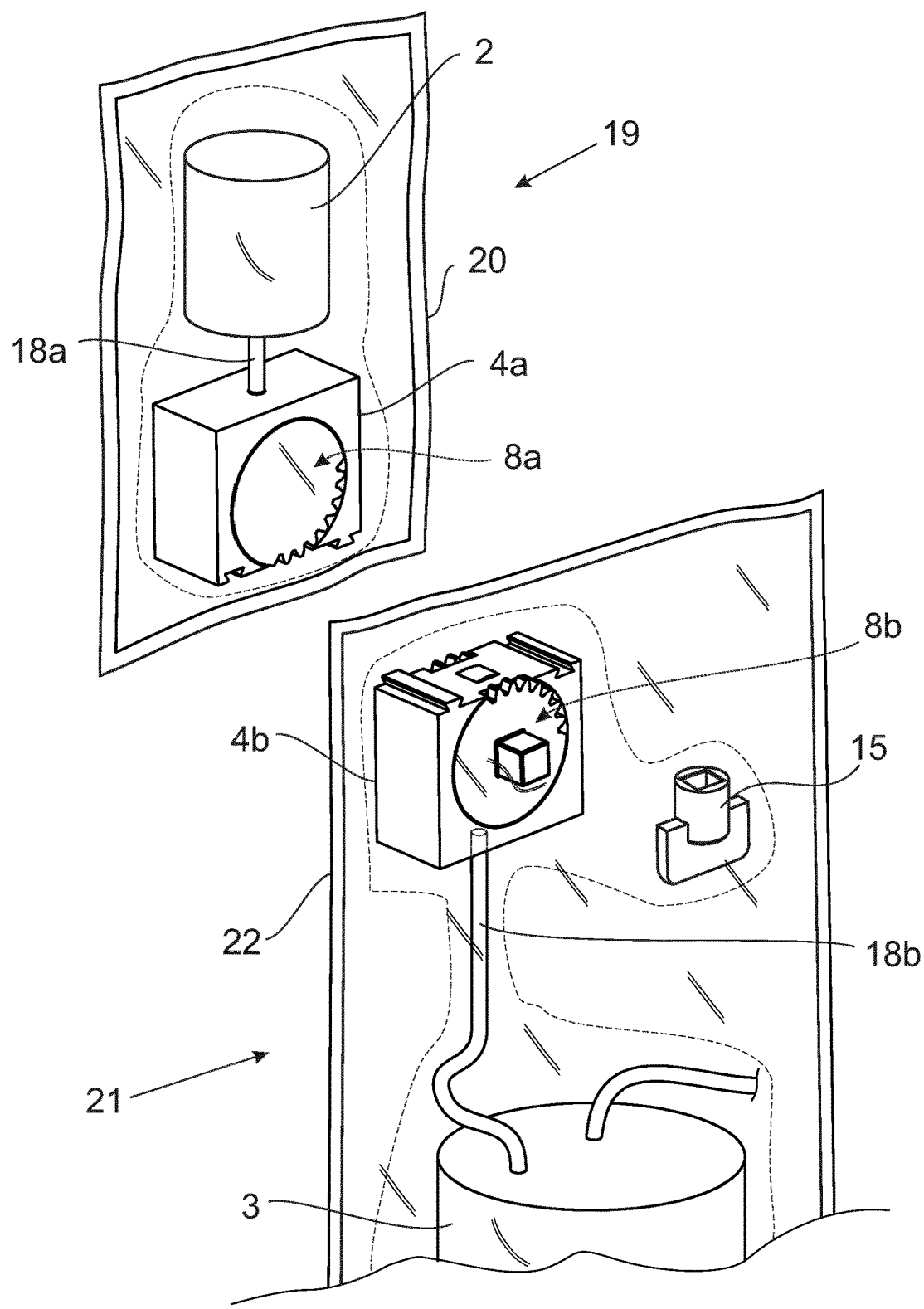
FIG. 4 shows, in a perspective view, a proposed packaging arrangement having a proposed coupling device and a liquid container connected thereto, and a proposed packaging arrangement having a further proposed coupling device and a bioprocess engineering system connected thereto.

According to one exemplary embodiment, there is provided a packaging arrangement 19 as is shown at the top in FIG. 4, having a packaging 20 and a proposed coupling device 4a sterile packaged therein and a liquid container 2, in particular a filled liquid container, here a liquid container that has already been filled by the manufacturer, sterile packaged therein. The liquid container 2 is thereby fluidically coupled with the proposed coupling device 4a of the sterile connector 1, that is to say already in the packaged state, and the control element 8a of the coupling device 4a is thereby in its starting position.

According to a further exemplary embodiment, there is provided a packaging arrangement 21 as is shown at the bottom in FIG. 4, having a packaging 22 and a proposed coupling device 4b sterile packaged therein and a bioprocess engineering system 3, here a bioreactor, sterile packaged therein. The bioprocess engineering system 3, or bioreactor, is thereby fluidically coupled with the proposed coupling device 4b of the sterile connector 1, that is to say in the packaged state, and the control element 8b of the coupling device 4b is in its starting position. Here, the packaging arrangement 21 additionally also has an actuating element 15, which is later used, in the assembled state of the sterile connector 1, that is to say when the housings 5a, 5b are connected together as described, for manually actuating the transmission 14 and accordingly for adjusting the control elements 8a, 8b from the starting position into the operating position.

In an alternative exemplary embodiment not shown here, there is also conceivable a packaging arrangement having a packaging in which only a proposed sterile connector 1, comprising both coupling devices 4a, 4b, is sterile packaged. In principle, it is also conceivable to provide a packaging arrangement in which only the respective coupling device 4a, 4b is sterile packaged.

According to various embodiments, the use of a sterile packaged proposed sterile connector 1, of a sterile packaged proposed coupling device 4a, 4b and/or of a proposed packaging arrangement 19, 21 for the sterile transfer of a liquid medium, in particular a biological medium, from a liquid container 2 to a bioprocess engineering system 3, in particular to a bioreactor, is provided. In this respect, as regards the provided use too, reference may be made to all remarks concerning the proposed sterile connector 1, the proposed coupling device 4a, 4b and the proposed packaging arrangement 19, 21.

According to the exemplary embodiment shown in FIG. 4, after the unit comprising the coupling device 4a and the liquid container 2 has been unpacked, on the one hand, and after the unit comprising the coupling device 4b and the bioprocess engineering system 3 has been unpacked, on the other hand, one coupling device 4a is connected to the other coupling device 4b as described, in each case with the flexible tubes 18a, 18b or the pipes producing the connection. The control elements 8a, 8b are then adjusted, in particular synchronously, from their starting position into their operating position, so that the transfer of the liquid medium from the liquid container 2 via the coupling device 4a and the coupling device 4b to the bioprocess engineering system 3 can then take place.

In some embodiments, at least the proposed coupling device 4a or the proposed coupling device 4b, in particular both coupling devices 4a, 4b, in some embodiments also the liquid container 2 and/or the bioprocess engineering system 3 and/or the flexible tube(s) 18a, 18b or the pipe(s) is/are in each case a single-use component. Each component, that is to say each coupling device 4a, 4b, the liquid container 2, the bioprocess engineering system 3 and/or each flexible tube 18a, 18b or each pipe, is produced at least in part, in some embodiments at least predominantly, from a plastics material. Suitable plastics materials for the individual components are in particular a silicone material and/or a polymer material, in particular an elastomer and/or thermoplastic and/or Vero material. Examples thereof are PE (polyethylene), PP (polypropylene), PTFE (polytetrafluoroethylene), PBT (polybutylene terephthalate), PSU (polysulfone), PESU (polyethersulfone), PC (polycarbonate).

The invention claimed is:

1. A sterile connector for the sterile transfer of a liquid medium from a liquid container to a bioprocess engineering system,
   wherein the sterile connector has two coupling devices,
      wherein the coupling devices each have a housing having a housing interior and a control element which is adjustably mounted in the housing interior and forms a channel, wherein the channel extends through the control element from a control element inlet opening to a control element outlet opening,
      wherein the housing of one coupling device is configured to be mechanically connected to the housing of the other coupling device,
      wherein each housing has a fluid inlet and a fluid outlet which connect the housing interior to the surroundings, wherein, in the mechanically connected state of the housings, the fluid outlet of one housing and the fluid inlet of the other housing overlap,
      wherein, to produce a sterile fluid connection, in the mechanically connected state of the housings, the control elements are adjustable from a starting position, in which a fluid connection between the channel and the control element inlet opening on the one hand and between the channel and the control element outlet opening on the other hand is blocked, into an operating position, in which the control element inlet opening is fluidically connected to the fluid inlet and the control element outlet opening is fluidically connected to the fluid outlet,
      wherein, in the mechanically connected state of the housing, an adjusting movement of one of the control elements between the starting position and the operating position is accompanied by a corresponding adjusting movement of the other control element, wherein a gear train is provided, which, in the mechanically connected state of the housings, effects a synchronous adjustment of the two control elements between the starting positions and the operating positions.

2. The sterile connector as claimed in claim 1, wherein, in the starting position, each channel extends in a region of the housing interior that is hermetically sealed with respect to the surroundings of the housing.

3. The sterile connector as claimed in claim 2, wherein, in the starting position, the control element inlet opening and the control element outlet opening each face the housing inner wall of the respective housing.

4. The sterile connector as claimed in claim 1, wherein, in the starting position, a portion of the respective control element closes the fluid inlet and/or a portion of the respective control element closes the fluid outlet of the respective housing in a hermetically tight manner, and/or
wherein, in the starting position, a portion of the respective control element extending around the control element inlet opening and/or a portion of the respective control element extending around the control element outlet opening is in contact in a hermetically sealing manner with the housing inner wall of the respective housing, and/or
wherein, in the starting position, a portion of the respective housing extending around the fluid inlet and/or a portion of the respective housing extending around the fluid outlet is in contact in a hermetically sealing manner with the respective control element.

5. The sterile connector as claimed in claim 1, wherein the control element of one housing projects from the housing interior through the fluid outlet of the housing, and/or wherein the control element of the other housing projects from the housing interior through the fluid inlet of the housing.

6. The sterile connector as claimed in claim 1, wherein the control element of one housing and the control element of the other housing, in the mechanically connected state of the housings, at least when the two control elements are in their operating position, are in contact with one another under preload.

7. The sterile connector as claimed in claim 1, wherein, in the mechanically connected state of the housings, when the two control elements are in their operating position, a portion of one control element extending around the control element outlet opening and a portion of the other control element extending around the control element inlet opening are in contact with one another in such a manner that the respective channel is hermetically sealed with respect to the respective housing.

8. The sterile connector as claimed in claim 1, wherein each control element is produced in part or completely, from an elastomer, and/or wherein each housing is produced in part from an elastomer.

9. The sterile connector as claimed in claim 1, wherein, in the mechanically connected state of the housings, when the two control elements are in their operating position, in the case of both coupling devices in each case the fluid inlet and the control element inlet opening and/or the fluid outlet and the control element outlet opening overlap and the fluid outlet of one housing and the fluid inlet of the other housing overlap.

10. The sterile connector as claimed in claim 9, wherein, in the mechanically connected state of the housings, when the two control elements are in their operating position, the two fluid inlets, the two fluid outlets and the two channels are oriented coaxially with one another.

11. The sterile connector as claimed in claim 1, wherein the adjusting movement of each control element between its starting position and its operating position is a rotational movement.

12. The sterile connector as claimed in claim 1, wherein the adjusting movement of each control element between its starting position and its operating position is limited in the starting position and/or operating position via a stop.

13. The sterile connector as claimed in claim 1, wherein the fluid inlet of one housing and the fluid outlet of the other housing is configured to be connected or is connected to a flexible tube or a pipe for the delivery of the liquid medium, and/or wherein the fluid outlet of the other housing is fluidically coupled via the flexible tube or the pipe with the bioprocess engineering system.

14. The sterile connector as claimed in claim 1, wherein the two housings are configured to be connected together in a form-fitting manner.

15. A packaging arrangement having a packaging and having the sterile connector as claimed in claim 1 sterile packaged therein.

16. The packaging arrangement as claimed in claim 15, wherein the control element of the coupling device sterile packaged in the packaging is in its starting position, and wherein there is additionally sterile packaged in the packaging the liquid container, which is fluidically coupled with the coupling device, or there is sterile packaged the bioprocess engineering system which is fluidically coupled with the coupling device.

17. A method of transferring liquid medium using the packaging arrangement as claimed in claim 15, for the sterile transfer of the liquid medium from the liquid container to the bioprocess engineering system comprising:
removing the packaging,
after removing the packaging, mechanically connecting the housings to one another,
after mechanically connecting the housings, adjusting the control elements each from the starting position, in which the fluid connection between the channel and the control element inlet opening on the one hand and between the channel and the control element outlet opening on the other hand is blocked, into the operating position, in which the control element inlet opening is fluidically connected to the fluid inlet and the control element outlet opening is fluidically connected to the fluid outlet, and
transferring the liquid medium from the liquid container to the bioprocess engineering system when in the operating position of the control elements.

18. The method as claimed in claim 17, wherein at least one of the coupling devices is produced at least in part from a plastics material.

19. A coupling device of a sterile connector for the sterile transfer of a liquid medium from a liquid container to a bioprocess engineering system,
wherein the coupling device has a housing having a housing interior and a control element which is adjustably mounted in the housing interior and forms a channel, wherein the channel extends through the control element from a control element inlet opening to a control element outlet opening,
wherein the housing of the coupling device is configured to be mechanically connected to the housing of a further coupling device of the sterile connector, wherein the housing has a fluid inlet and a fluid outlet which connect the housing interior to the surroundings, wherein, in the mechanically connected state of the housings, the fluid outlet of the housing of the coupling device and the fluid inlet of the housing of the further coupling device are configured to be brought to overlap, wherein, to produce a sterile fluid connection, in the mechanically connected state of the housings, the control element is adjustable from a starting position, in which a fluid connection between the channel and the control element inlet opening on the one hand and between the channel and the control element outlet opening on the other hand is blocked, into an operating position, in which the control element inlet opening is fluidically connected to the fluid inlet and the control element outlet opening is fluidically connected to the fluid outlet, wherein, in the mechanically connected state of the housing, an adjusting movement of one of the control elements between the starting position and the operating position is accompanied by a corresponding adjusting movement of the other control element, wherein a gear train is provided, which, in the mechanically connected state of the housings, effects a synchronous adjustment of the two control elements between the starting positions and the operating positions.

* * * * *